(12) United States Patent
Wijitphan

(10) Patent No.: US 7,485,309 B1
(45) Date of Patent: Feb. 3, 2009

(54) METHOD TO STIMULATE RESIN FORMATION BY WOUNDING ON THE AQUILARIA'S TRUNK

(76) Inventor: Pheeraphan Wijitphan, 126/2050 Tiwanon, Soi 19/1 Parkkret, Nonthaburi 11120, Bangkok (TH)

( * ) Notice: Subject to any disclaimer, the term of this patent is extended or adjusted under 35 U.S.C. 154(b) by 677 days.

(21) Appl. No.: 10/807,665

(22) Filed: Mar. 24, 2004

(51) Int. Cl.
*A61K 36/00* (2006.01)

(52) U.S. Cl. .................... 424/195.18; 424/769; 424/775

(58) Field of Classification Search ................ None
See application file for complete search history.

(56) References Cited

U.S. PATENT DOCUMENTS

| | | | |
|---|---|---|---|
| 6,848,211 B2 * | 2/2005 | Blanchette et al. ....... | 47/58.1 R |
| 2002/0194780 A1 * | 12/2002 | Blanchette et al. ............... | 47/8 |
| 2005/0008657 A1 * | 1/2005 | Blanchette et al. ..... | 424/195.18 |

* cited by examiner

*Primary Examiner*—Christopher R Tate
*Assistant Examiner*—Deborah A. Davis
(74) *Attorney, Agent, or Firm*—Michael I. Kroll

(57) ABSTRACT

This invention is mainly about the making of wounds on the Aquilaria's trunk in order to stimulate the process of Aquilaria resin formation. The wounds in this invention include details of wounds made on the Aquilaria's trunk with the specifications of shape, location, size, beveling, gouging, making holes, and the method of leading the stimulant to Aquilaria through the wounds. The details are shown in this invention. The methods begin with the selection of Aquilaria trees, which have a diameter of about 50 centimeters. Then make a square shaped wound on the trunk with the size and position as specified in the details of the invention. The rims will be gouged as the small channel. Inside the square, make many holes deep into the heartwood. These holes will stimulate Aquilaria to release resin and it is easier to use the stimulant to merge the wounds. In proper time, the resin can be collected and used for further benefits.

2 Claims, 8 Drawing Sheets

METHOD TO STIMULATE RESIN FORMATION BY WOUNDING ON THE AQUILARIA'S TRUNK

BACKGROUND OF THE INVENTION

1. Field of Science Related to the Invention

This invention basically involves with making wounds on the Aquilaria's trunk to stimulate the Aquilaria resin formation.

2. Related Background of Knowledge or Science

Aquilaria is a tree that can produce resin, which has a pleasant scent widely used. However, some kinds of Aquilaria cannot create such resin or can produce the resin in a small quantity. Some kinds of Aquilaria can produce the resin in a high quantity but the scientists still lack the suitable method to stimulate and collect the resin in terms of commerce. This invention reveals the effective solutions to the problems mentioned above as shown in the details of the invention.

CHARACTERISTICS AND GOALS OF THE INVENTION IN BRIEF

This invention was the consistent attempt of the inventor in studying the process of Aquilaria resin formation in Southeast Asia and South Asia regions for many years. The inventor found that not all kinds of Aquilaria can produce the resin. Some kinds of Aquilaria can produce the resin in a high quantity such as Aquilaria Crassna Pierre, Aquilaria Subintegra Ding Hau, Aquilaria Malaccensis Roxb. and the new breed combined between the two kinds called Aquilaria Phanraphee That, which was originally developed by the inventor.

This invention is mainly about wounding on the Aquilaria's trunk in order to stimulate the process of Aquilaria resin formation. The wounds in this invention include details of wounds made on the Aquilaria's trunk with the specification of shape, location, size, beveling, gouging, making holes, and the method of leading the stimulant to Aquilaria through the wounds. The details are shown in this invention.

The method begins with the selection of Aquilaria trees, which have the diameter about 50 centimeters. Then, make a square shape wound on the trunk with the size and position as specified in the details of the invention. The rims will be gouged as the small channel. Inside the square, make many holes deep into the heartwood. These wounds will stimulate Aquilaria to release resin and it is easier to use the stimulant to merge the wounds. In the proper time, the resin can be collected and used for further benefits.

However, when we mention about the method of using the stimulant to Aquilaria or leading the stimulant to Aquilaria, there has never been a process, which is similar to this invention. The inventor will not reveal the details of stimulant and this invention does not hold the right of such stimulant.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
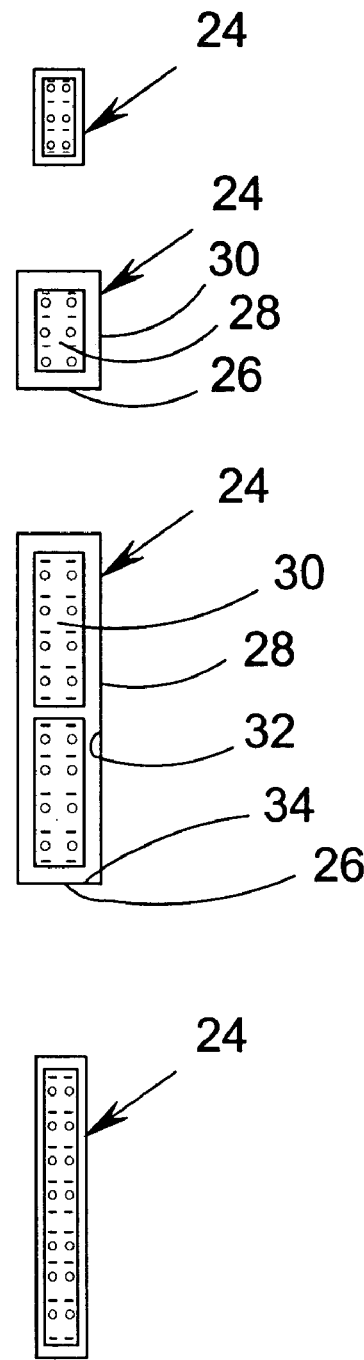
FIG. 1 shows the wounds made on the trunk of Aquilaria, which can be done in many shapes.
Figure 2:
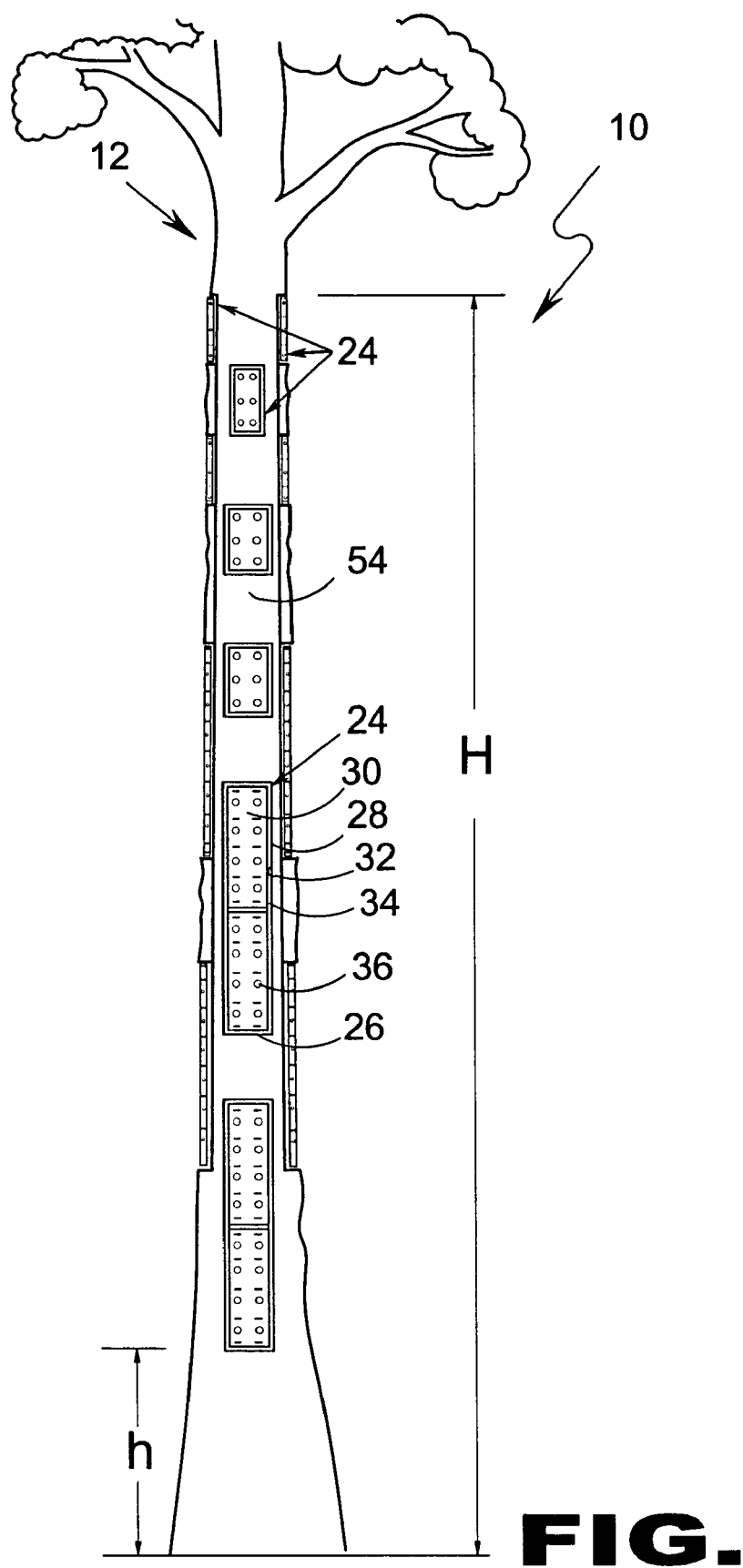
FIG. 2 shows how to make wounds on the trunk of Aquilaria in the suitable positions on the trunk.
Figure 3:
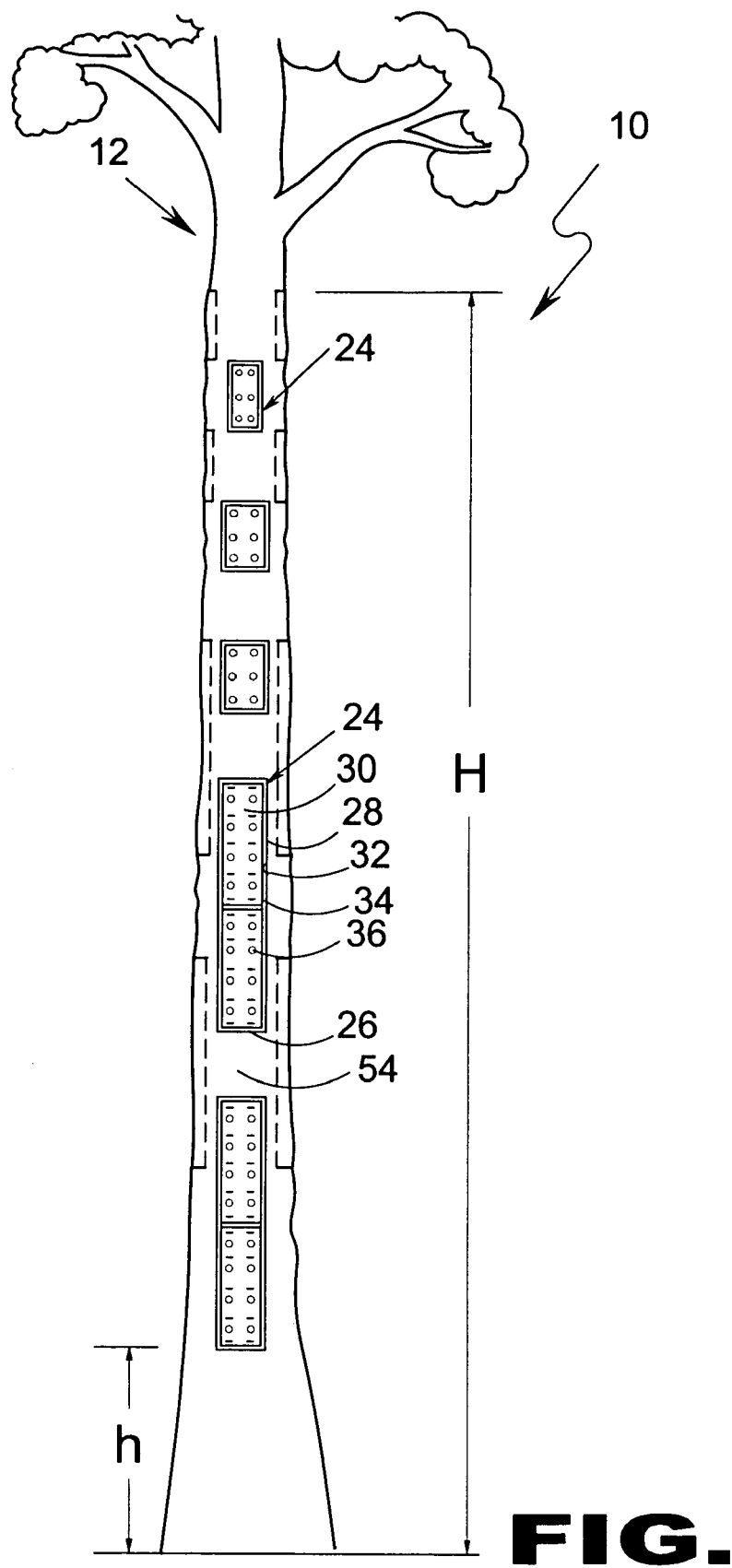
FIG. 3 shows how to make wounds on the front of the trunk of Aquilaria.
Figure 4:
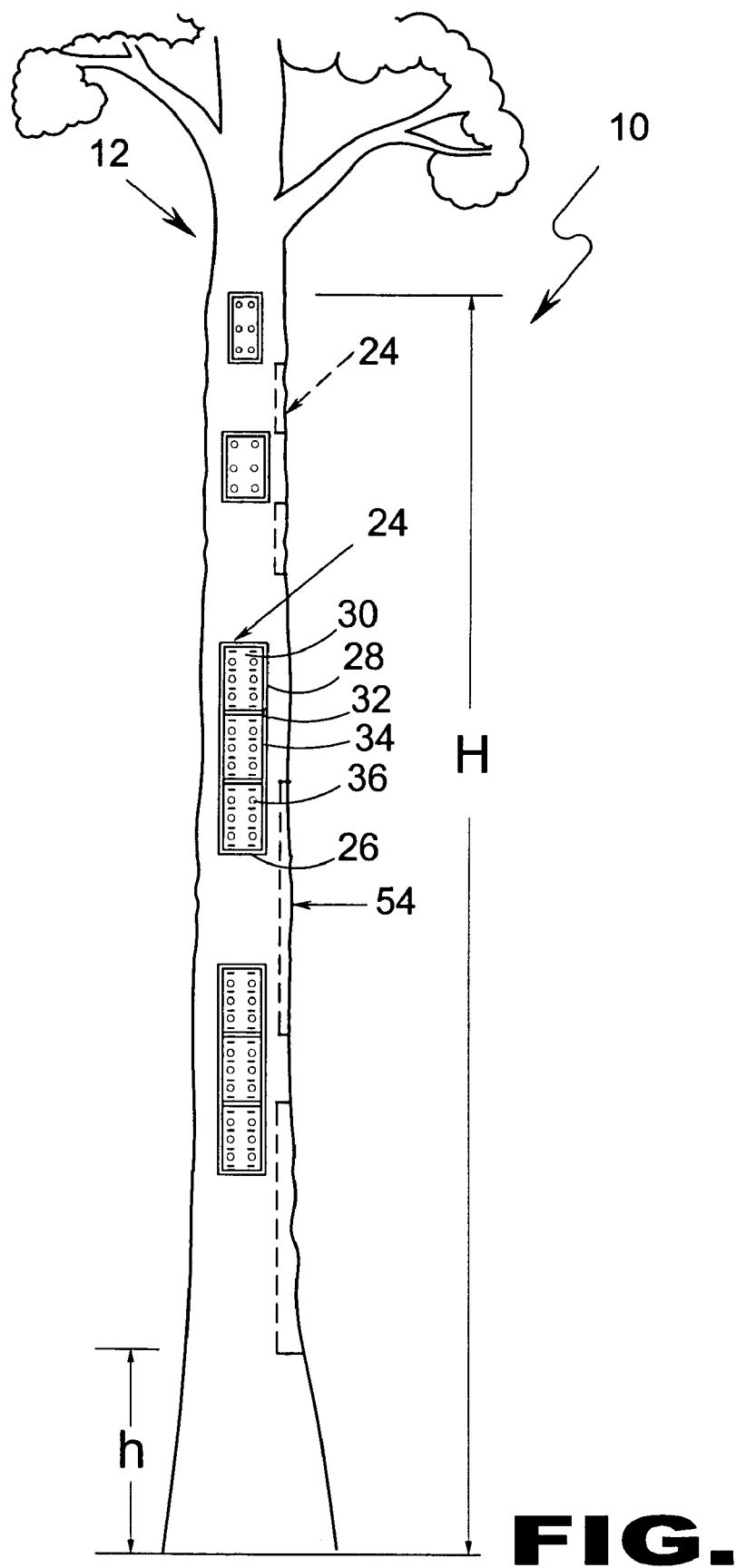
FIG. 4 shows how to make wounds on the side of the trunk of Aquilaria.
Figure 5:
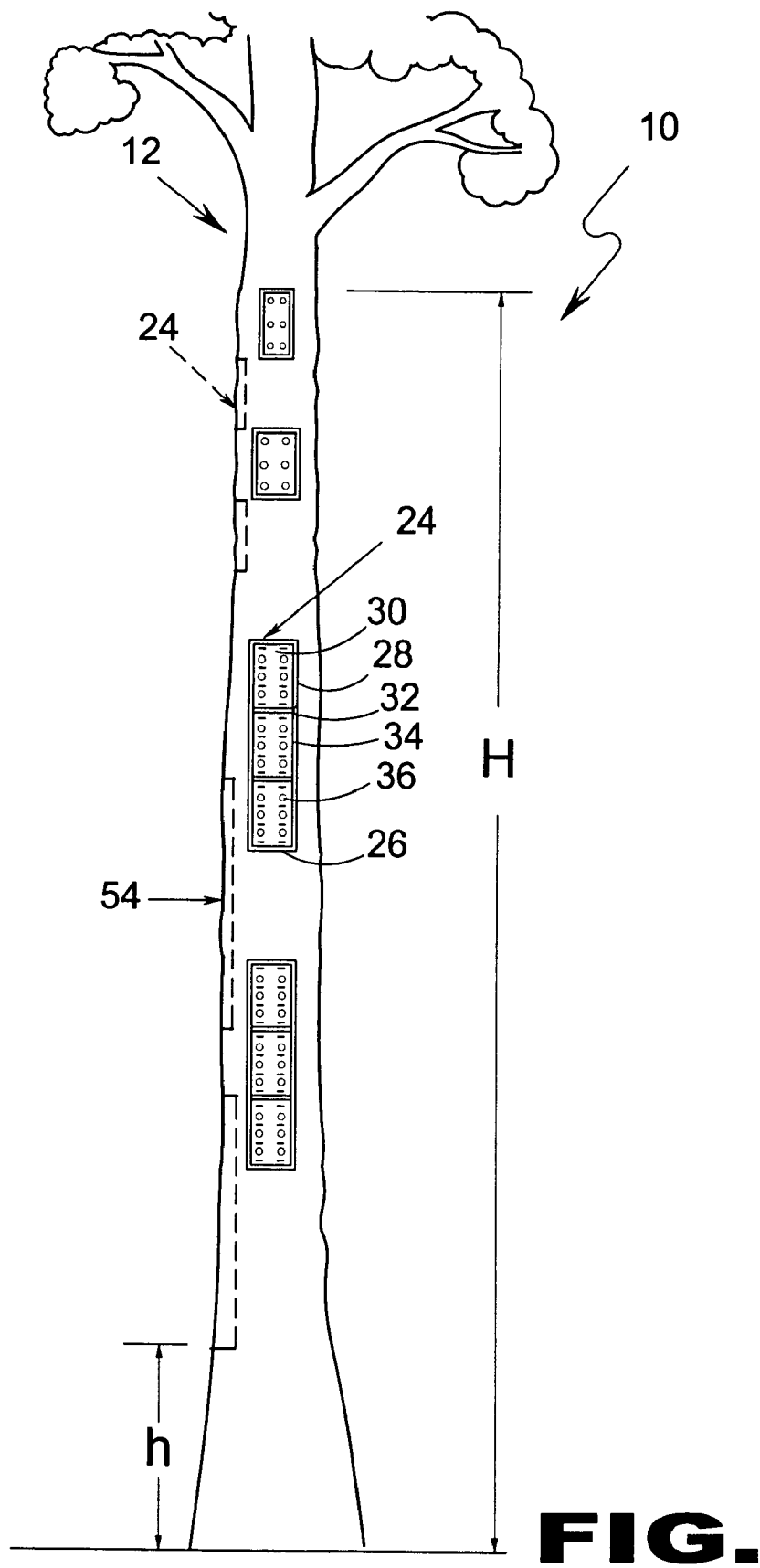
FIG. 5 shows how to make wounds on the other side of the trunk of Aquilaria.

Turning now descriptively to the drawings, in which similar reference characters denote similar elements throughout the several views, the Figures illustrate the method for inducing resin production of the present invention. With regard to the reference numerals used, the following numbering is used throughout the various drawing figures.

10 method of stimulating the formation of resin
12 Aquilaria
14 cross section of the trunk
16 the minimum diameter
18 the minimum height
20 the maximum height
22 resin formation
24 wounds
26 width of wounds
28 length of wounds
30 depth of wounds
32 width of channel
34 channel
36 holes
38 width of holes
40 depth of holes
42 outer bark
44 phloem
46 meristemetic tissues
48 sapwood
50 heartwood
52 pith
54 the front of tree
56 girth cut
58 root
60 making holes at the root

DETAILED DESCRIPTION OF THE PREFERRED EMBODIMENT

The explanation from now on will refer to the drawings in order to help readers to understand the innovation clearer and these drawing are considered partial to this innovation by not limiting the scope of innovation. Experts in this field may apply any function of this innovation to their professional operation.

According to FIG. 1, it shows how to make wounds on the trunk of Aquilaria including the making of wounds (24) by taking off the outer layer (42) and the tissue in square shape with the width (26) length (28) depth (30) suitable to the size of the trunk that will not affect the growth or cause death to the tree. An example of ratio that the inventor suggested since it is appropriate size and convenient to mark the position on the tree is by specifying the width (26) at 10-15 centimeters, length (28) at 20-75 centimeters and the depth (30) 1-3 centimeters. Inside the square frame, there are many holes (36)

deep into the heartwood. The shape of holes (36) can be circular or any kind of square with the size of holes (36) that will not harm the trees and the size should allow the stimulant to penetrate Aquilaria. An example of the size is the diameter of hole (36) at 0.5-2 centimeters and area around the wounds will be cut as channel (34).

Positioning the wounds on Aquilaria from Picture 2-5 shows the position of wounds of Aquilaria. Even though resin can be produced in almost every part of Aquilaria, the inventor found that 5-9 year old Aquilaria with approximately 35-55 centimeters in diameter (6) is suitable to make wounds on the trunk with the height from the ground (h) about 50-70 centimeters. The suitable height is from 60 centimeters up to 500 centimeters. The height (H) that is convenient for workers is 310 centimeters.

Besides positioning the wounds on Aquilaria as shown, FIGS. 2-5 also shows the positions of wounds around the trunk. The wounds in the front and sides should be done at different levels and it has been found that such positions do not harm Aquilaria.

After finishing the above process, it will take a long time for the resin formation. Therefore, the innovator created the method of leading the stimulant to Aquilaria through the wounds to get resin and it has found that the stimulant penetrated into the tree quite well while producing resin in a shorter time.

Figure 6:
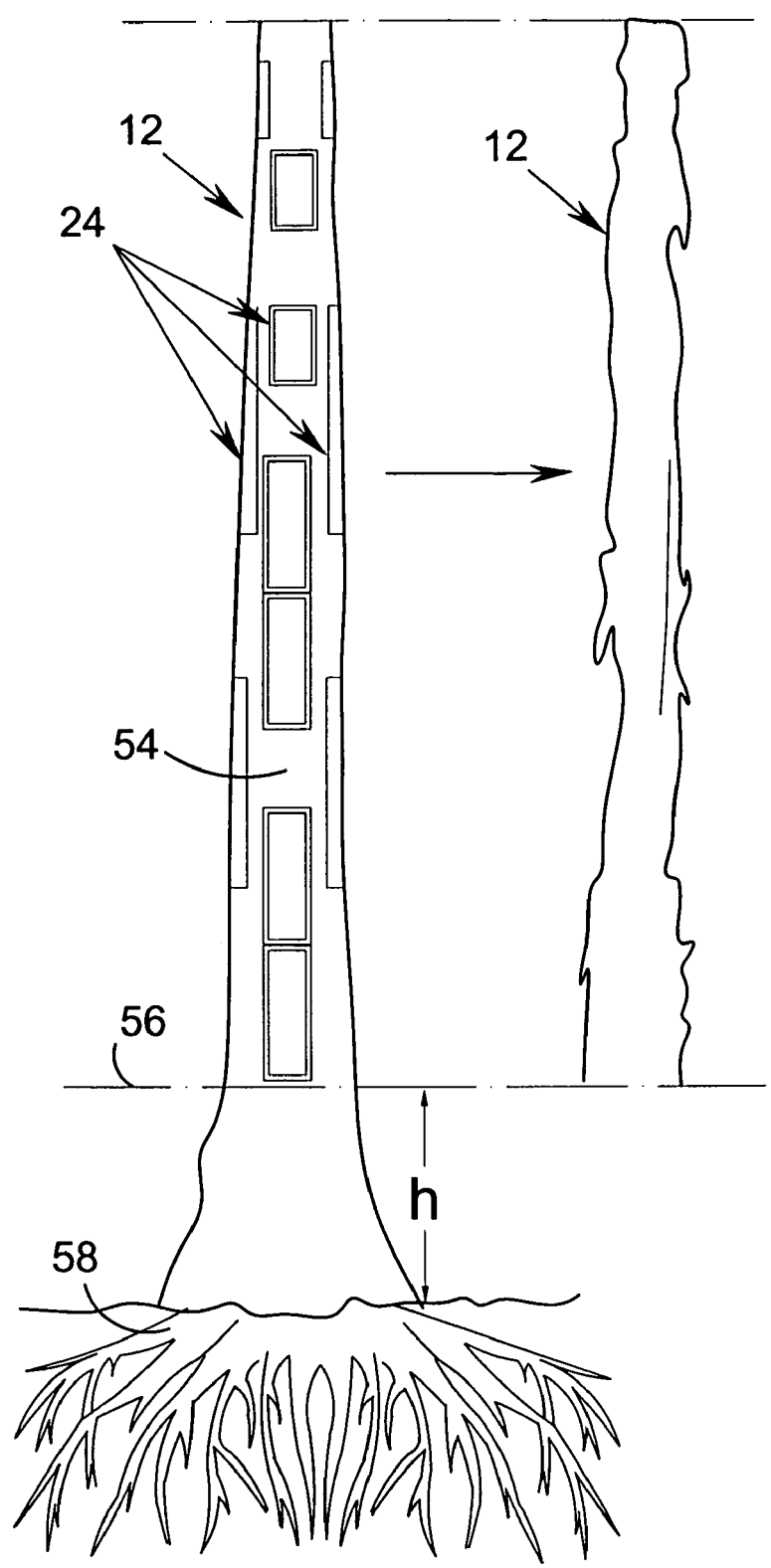
FIG. 6 shows the process of resin extraction from 8-9 year old Aquilaria by cutting on the trunk about 50-60 centimeters high from the ground.

When Aquilaria reach 8-9 years old, the resin can be collected. In FIG. 6, it shows the cross section of the trunk of Aquilaria at the height from ground (h) 50-70 centimeter, while the suitable level is 60 centimeters. It has been found that the area being stimulated, which is in the level of (h) to (H) gives more resin than other positions.

Figure 7:
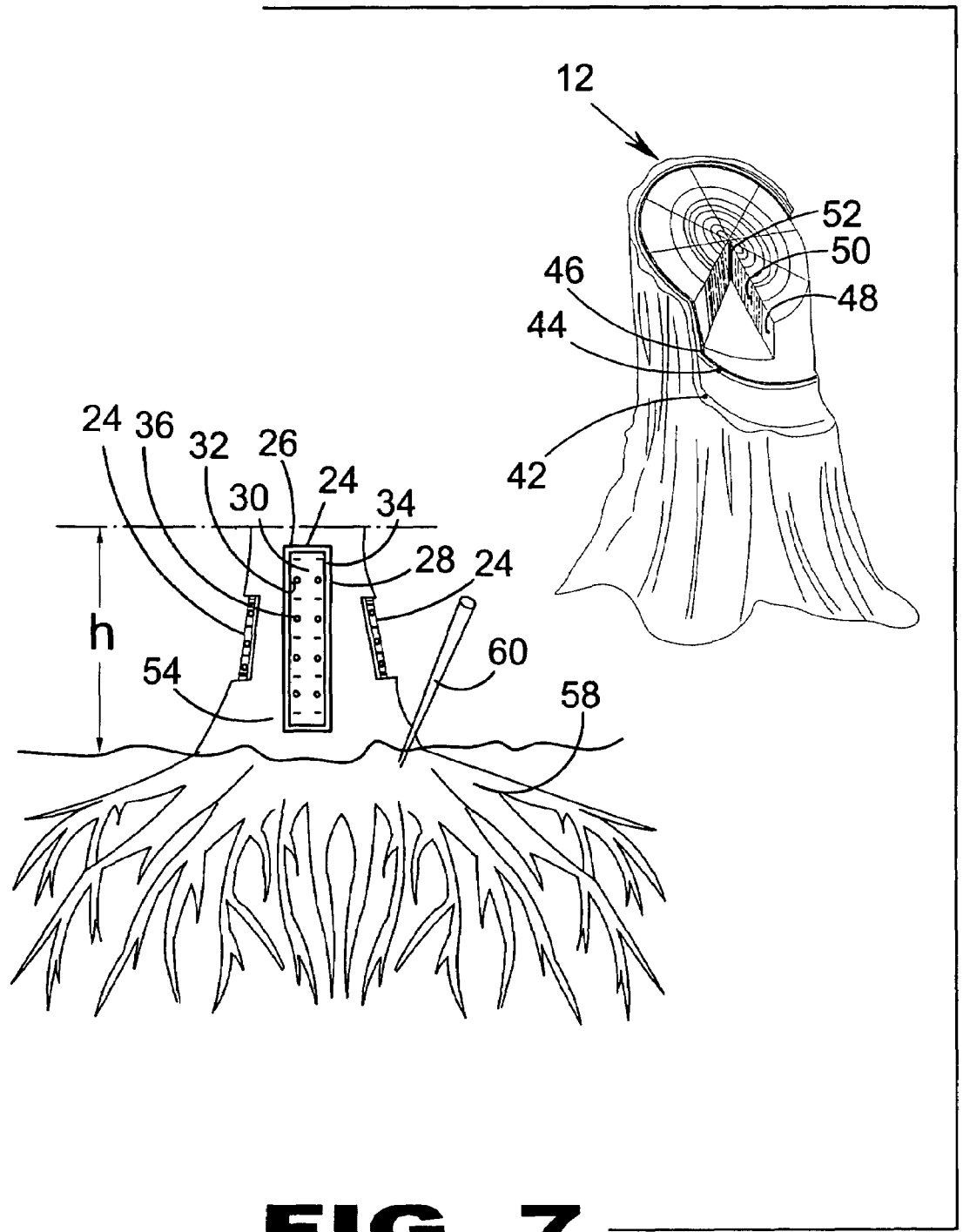
FIG. 7 shows the stimulation on the stump of Aquilaria by making wounds as mentioned in this invention.
Figure 8:
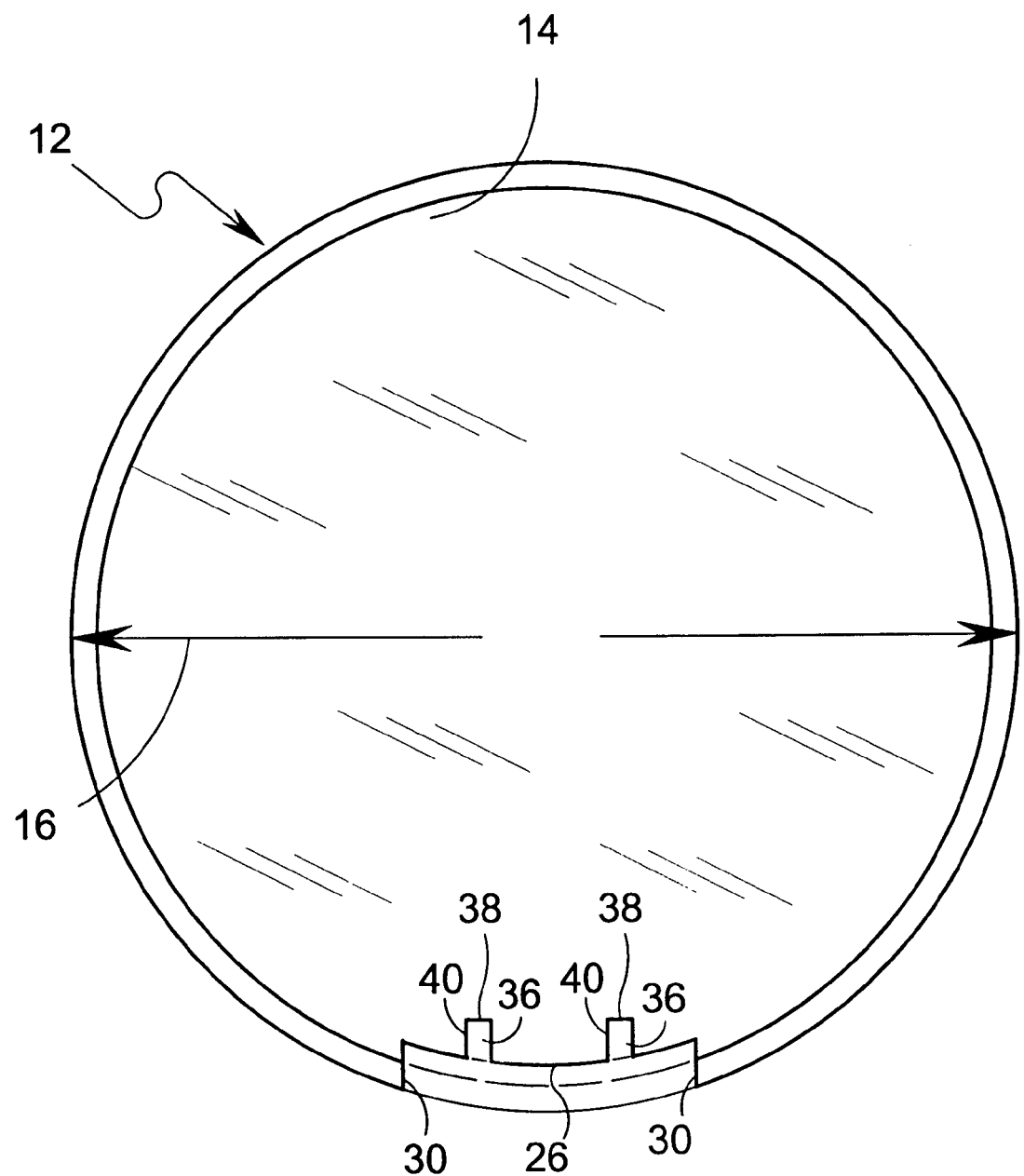
FIG. 8 shows the cross section of the suitable size of Aquilaria trunk to be stimulated.

Surprisingly, the innovator found that the stump left after being cut down can be kept for another 6-15 years and can be stimulated to produce resin. In FIG. 7, it shows how to make wounds by using the same technique and also includes the method of making holes (60) at the root (58). After discovering that the stump can produce a high quantity of resin, making holes (60) at the roots (58) is the method that let the stump die slowly and accumulate the resin in high quantity, which is enough for extraction.

I claim:
1. A method of stimulating the process of Aquilaria resin formation by making wounds on the Aquilaria's trunk consisting of:
   a) Selecting Aquilaria aged between 5-9 years old with 35-55 centimeters in diameter of the trunk;
   b) Making a number of wounds on said Aquilaria trunk each wound made by removing an outer layer forming rectangular shaped wounds;
   c) Cutting a channel around each rectangular wound;
   d) Drilling a plurality of holes within each rectangular wound deep into heartwood of said Aquilaria; and
   e) Collecting Aquilaria resin from said holes.
2. A method of stimulating the process of Aquilaria resin formation comprising the steps of:
   a) making a plurality of wounds on a stump of a cut down Aquilaria by removing an outer layer forming rectangular shaped wounds;
   b) drilling a plurality of holes within each rectangular wound deep into heartwood of said Aquilaria;
   c) cutting a channel around each wound; and
   d) making a hole at a root of said Aquilaria to allow the stump to die slowly and accumulate the resin from said hole.

* * * * *